United States Patent [19]

Kovacs

[11] Patent Number: 5,580,435
[45] Date of Patent: Dec. 3, 1996

[54] SYSTEM FOR DETECTING COMPONENTS OF A SAMPLE IN ELECTROPHORETIC SEPARATION

[75] Inventor: Gregory T. A. Kovacs, Stanford, Calif.

[73] Assignee: The Board of Trustees of the Leland Stanford Junior University, Palo Alto, Calif.

[21] Appl. No.: 258,849

[22] Filed: Jun. 10, 1994

[51] Int. Cl.$^6$ ................................................. G01N 27/26
[52] U.S. Cl. ........................ 204/603; 204/451; 204/452; 204/601; 73/61.58
[58] Field of Search ........................ 204/299 R, 180.1, 204/409; 324/450, 439; 73/61.58

[56] References Cited

U.S. PATENT DOCUMENTS

| | | | |
|---|---|---|---|
| 3,051,631 | 8/1962 | Harbin, Jr. et al. | 324/450 |
| 3,932,264 | 1/1976 | Haruki et al. | 204/299 R |
| 4,061,560 | 12/1977 | Kobayashi | 204/299 R |
| 4,459,198 | 7/1984 | Mizuno | 204/299 R |
| 4,891,120 | 1/1990 | Sethi et al. | 204/299 R |
| 4,908,112 | 3/1990 | Pace | 204/299 R |
| 5,126,023 | 6/1992 | Huang et al. | 204/180.1 |
| 5,194,133 | 3/1993 | Clark et al. | 204/299 R |
| 5,223,114 | 6/1993 | Zare et al. | 204/180.1 X |
| 5,296,114 | 3/1994 | Manz | 204/180.1 |

FOREIGN PATENT DOCUMENTS

| | | | |
|---|---|---|---|
| 241940 | 10/1987 | European Pat. Off. | 204/299 R |
| 2191110 | 10/0000 | United Kingdom . | |

OTHER PUBLICATIONS

"On–Column Conductivity Detector for Capillary Zone Electrophoresis," by Huang et al., Anal. Chem., vol. 59, pp. 2747–2749, Dec. 1987.

"Improved End–Column Conductivity Detector for Capillary Zone Electrophoresis," by Huang et al., Anal. Chem., vol. 63, pp. 2193–2196, Oct. 1991.

"Preparation of Strongly Adherent Platinum Black Coatings," by Marrese, Anal. Chem., vol. 59, pp. 217–218, Jan. 1987.

"Towards Miniaturized Electrophoresis and Chemical Analysis Systems on Silicon: An Alternative to Chemical Sensors," by Harrison et al., Sensors and Actuators, vol. 10, pp. 107–116, no month available 1993.

"Synchronized Cyclic Capillary Electrophoresis A Novel Approach to Ion Separations in Solution," by Burggraf et al., The 7th International Conference on Solid–State Sensors and Actuators, pp. 399–406 no date.

"Microfabricated Electrochemical Detector for Capillary Electrophoresis," by Kovacs et al. no date.

"Miniaturized Chemical Analysis Systems Based on Electrophoretic Separations and Electroosmotic Pumping," by Harrison et al., The 7th Invernational Conference on Solid–State Sensors and Actuators, pp. 403–406. no date.

*Primary Examiner*—John Niebling
*Assistant Examiner*—John S. Starsiak, Jr.
*Attorney, Agent, or Firm*—Majestic, Parsons, Siebert & Hsue

[57] ABSTRACT

A substrate defines a group therein having three sections: a first and third sections having dimensions larger than the outside dimensions of two capillaries and a second section separating the first and third sections with dimensions small than the outside dimensions of the capillaries. When the two capillaries are inserted into the first and third sections and capillary electrophoretic separation performed in one or both of the capillaries, the separated components may be detected using a pair of detectors located at the second section. The electrodes are electrically isolated from an analysis or storage device used to analyze or store signals at the electrodes.

24 Claims, 4 Drawing Sheets

SYSTEM FOR DETECTING COMPONENTS OF A SAMPLE IN ELECTROPHORETIC SEPARATION

BACKGROUND OF THE INVENTION

This invention relates in general to sample component detection in systems for sample separation and analysis and in particular to detection systems in electrophoretic separation.

Capillary electrophoresis (CE) is a powerful analytical separation technique for the analysis of complex mixtures. In CE, an unknown sample is introduced at an inlet of a capillary channel filled with a buffer solution, and a high voltage is applied across a section of the capillary. Different constituents of the sample migrate through the capillary at different rates depending on their electrophoretic mobilities. Mobility is a complex function of a particle's charge, mass, and shape in solution. A difference in mobilities allows separation of the sample into its components. By detecting the chemicals passing through a part of the capillary or its outlet as a function of time, and knowing the mobilities of the possible constituents, the chemical composition of the sample can be determined.

A number of detectors have been developed for CE, including absorbance, fluorescence, mass-spectrometric and electrochemical methods. Electrochemical detection has certain advantages including sensitivity and selectivity for individual species. Several different types of electrochemical detection can be used, including conductivity measurements, impedance spectroscopy, amperometry and voltammetry. Two key problems with electrochemical detection that need to be overcome are isolation of the detection apparatus from the 1 to 30 kV potential present, and rejection of power supply noise. If the electrodes are not precisely perpendicular to the fluid flow in the separation channel, a large noise signal may be coupled into the electrodes from the high voltage power supply. Another difficulty with previous electrochemical detectors is the irreproducible construction and inaccurate placement of the electrodes inside the separation column. It is therefore desirable to provide an improved detector that overcomes the above-described problems.

SUMMARY OF THE INVENTION

The detector of this invention enables the detection electrodes to be electrically isolated from the high separation voltage. Signals indicative of the separated components of the sample resulting from separation are conveyed for analysis in a manner that does not compromise the electrical isolation of the detector from the separation voltage.

One aspect of the invention is directed toward an apparatus for detecting components of a sample in a separation capillary containing a separation medium. The apparatus comprises a housing defining a tunnel therein. The tunnel has a first and a third section with cross-sectional dimensions larger than the outside dimensions of the capillary and a second section adjacent to and separating the first and third sections. The second section has cross-sectional dimensions smaller than the outside dimensions of the capillary. The apparatus further comprises one or more electrodes located at said second section, so that when each end of two capillaries is inserted into one of the first and third sections of the tunnel until said ends abut said second section and when a separation medium and a sample are introduced into the capillaries and the second section, said one or more electrodes is in electrical contact with said separation medium, said electrodes useful for detecting components of a sample in the medium and providing electrical signals indicative of these components.

Another aspect of the invention is directed towards an apparatus for electrophoretic separation of a sample and detection of the separated components. The apparatus comprises a capillary, a separation medium in the capillary, a power source, and a detector for detecting the separation components of the sample in the medium. The detector includes (a) a housing defining a tunnel therein, said tunnel having a first section with cross-sectional dimensions larger than the outside dimensions of the capillary and a second section adjacent to the first section, said second section having cross-sectional dimensions smaller than the outside dimensions of the capillary; and (b) one or more electrodes located at said second section, so that when one end of the capillary is inserted into the first section of the tunnel until said end abuts said second section and the medium is introduced into the second section, said one or more electrodes is in electrical contact with said separation medium, said electrodes useful for detecting components of a sample in the medium and for providing electrical signals indicative of the components. The apparatus further comprises a connector electrically connecting the medium in the second section to the source so that the power source applies an electrical potential between said portion and the medium in the second section to cause electrophoretic separation of the sample into its components, and so that said electrodes are substantially at a floating potential.

Yet another aspect of the invention is directed towards a method for separating a sample into its components and detection of the sample components, employing a capillary and a detector. The detector includes (a) a housing defining a tunnel therein, said tunnel having a first section with cross-sectional dimensions larger than the outside dimensions of the capillary and a second section adjacent to the first section, said second section having cross-sectional dimensions smaller than the outside dimensions of the capillary, and (b) one or more electrodes located at said second section. The method comprises the steps of: inserting one end of the capillary into the first section of the tunnel until said one end abuts said second section; introducing a separation medium into said second section and a portion of the capillary contiguous to the second section and connecting the medium in the second section and the medium in the portion of the capillary to a power source through a connector. The method further comprises the steps of: introducing a sample into the capillary and causing the source to apply an electrical potential across the medium in the second section and in said portion of the capillary to cause electrophoretic separation of the sample and so that the electrodes are substantially at a floating electrical potential; and detecting components of the sample in the medium passing the electrodes.

Still another aspect of the invention is directed towards a method for separation of a sample into its components and detection of the sample components. The method comprises the steps of: introducing a sample into a capillary channel containing a medium; applying an electrical field in a section of the channel to cause the sample to separate into its components; causing a pair of electrodes located across the channel to generate electrical signals in response to and indicative of the separated components; and transmitting information in the signals indicative of the separated components through an electrically non-conductive link to an analysis circuit. In the preferred embodiment, the link may be an optical or radio frequency link.

DETAILED DESCRIPTION OF THE PREFERRED EMBODIMENT

Figure 1A:
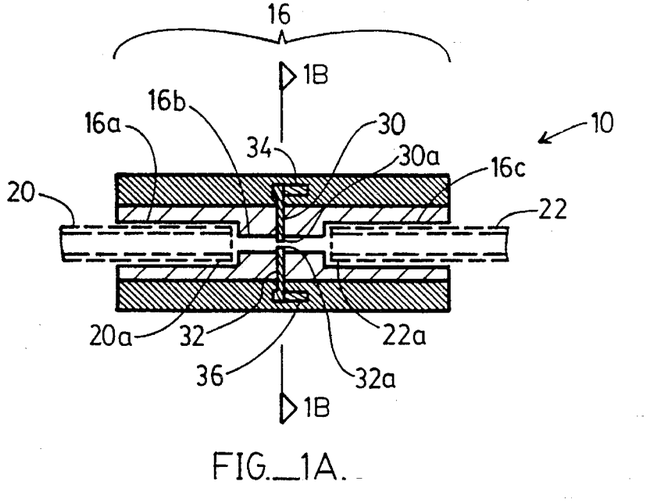
FIG. 1A is a top view of a detector useful for detecting the separating components in an electrophoretic device to illustrate the preferred embodiment of the invention.
Figure 1B:
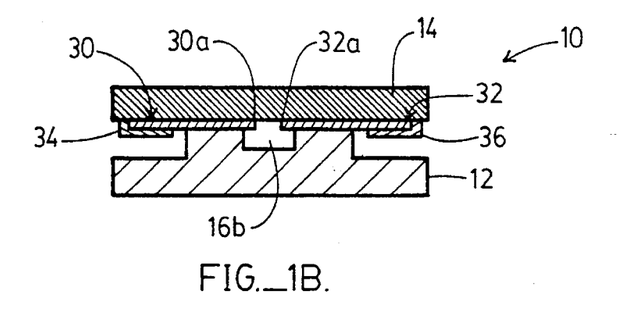
FIG. 1B is a cross-sectional view of the detector of FIG. 1A taken along the line 1B—1B in FIG. 1A.

FIG. 1A is a top view of a detector 10 that can be used in a capillary electrophoresis system to illustrate the preferred embodiment of the invention. FIG. 1B is cross-sectional view of the detector 10 of FIG. 1A taken along the line 1B—1B FIG. 1A. As shown in FIGS. 1A, 1B, detector 10 includes a substrate 12 defining a groove on its surface and a cover 14 in contact with the surface of the substrate covering the groove to form a tunnel 16. As shown in FIG. 1A, tunnel 16 has a first section 16a and a second section 16b and a third section 16c. The first and third sections 16a, 16c have cross-sectional dimensions larger than the outside dimensions of a capillary suitable for capillary electrophoresis. Shown in dotted lines FIG. 1A are two capillaries 20 and 22 with capillary 20 inserted into first section 16a and capillary 22 inserted into the third section 16c.

The cross-sectional dimensions of the second section 16b, however, are smaller than the outside dimensions of the capillary 20, 22 so that the ends 20a, 22a would abut section 16b when the capillary 20, 22 are inserted into the first and third sections as shown in FIG. 1A. The capillary 22 is omitted in FIG. 1B for simplicity. A pair of electrodes 30, 32 are placed at and in the second section 16b with their tips 30a, 32a directly across each other across the tunnel in the second section. Therefore, when sample components exit capillary 20 into section 16b, these components will affect the conductivity of the conductive medium within section 16b. Such change in conductivity may be detected by means of electrodes 30, 32. These components then enter capillary 22. A pair of bond pads 34, 36 are in contact respectively with electrodes 30, 32 for connecting the electrodes to outside circuitry. The top view in FIG. 1A is one through the transparent glass cover 14, so that the electrodes 30, 32 and the substrate below together with the tunnel are shown as visible in FIG. 1A.

Figure 1C:
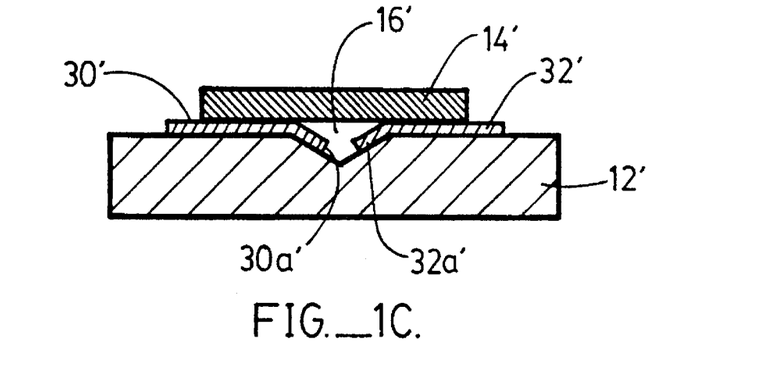
FIG. 1C is a cross-sectional view of the detector of FIG. 1A taken along the line 1B—1B in FIG. 1A to illustrate an alternative embodiment to that in FIG. 1B.

In the preferred embodiment shown in FIGS. 1A, 1B, electrodes 30, 32 and bond pads 34, 36 are in the form of layers on glass cover 14. It will be understood, however, that these may instead be fabricated on top of the substrate 12 instead; such configuration is shown in FIG. 1C. As shown in FIG. 1C, the tunnel 16' has a V-shaped cross-section etched into the surface of substrate 12'. Electrodes 30', 32' are layers on the surface of the substrate 12' extending into the V-shaped groove 16'. Glass cover 14' covers the groove to form the tunnel and parts of the electrodes, leaving parts of the electrodes exposed as bonding areas for bond wires. Such and other variations are within the scope of the invention.

Substrate 12 preferably includes or is made of a micromachinable material, such as a semiconductor material like silicon. If substrate 12 is made of silicon, the electrodes and bond pads may be fabricated using conventional semiconductor techniques. In the preferred embodiments, cover 14 is made of glass. It will be understood that device 10 may be constructed using a solid piece of material forming a housing by forming a tunnel 16 there through having the cross-sectional dimensions indicated in FIGS. 1A, 1B. Such and other variations are also within the scope of the invention.

In the preferred embodiments, sections 16a, 16c have cross-sectional dimensions in the range of about 50–350 microns. The second section preferably has cross-sectional dimensions in the range of about 25–325 microns.

Figure 2:
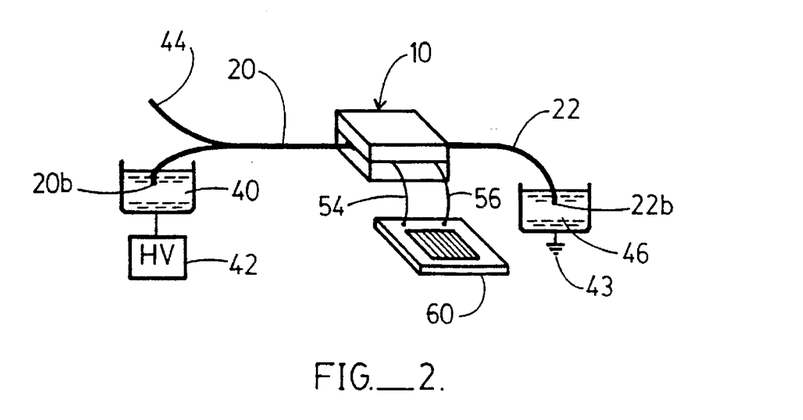
FIG. 2 is a block diagram of a capillary electrophoretic system using the detector of FIGS. 1A, 1B to illustrate the invention.

FIG. 2 is a block diagram of a capillary electrophoretic system employing detector 10 of FIGS. 1A, 1B to illustrate the invention. For simplicity in discussion, identical parts are labeled by the same numerals in the figures of this application. Capillaries 20, 22 are first inserted into sections 16a, 16c respectively until they abut section 16b. The capillaries and section 16b are then filled with an electrolyte buffer, such as by hydrostatic pressure difference across the capillary in a manner known to those skilled in the art. End 20b of capillary 20 is immersed in a buffer reservoir 40 connected electrically to a high voltage source 42, and end 22b of capillary 20 is immersed in a buffer reservoir 46 connected electrically to ground 43. Capillary 20 may also be connected to a sample injector (not shown) through a tube 44, such as through a T-connector known to those skilled in the art. Or, sample injection may be carried out through hydrostatic pressure.

When a sample is injected into capillary 20, such sample will undergo electrophoretic separation in the buffer due to the presence of the high electrical field in capillary 20. The separated components will then emerge from end 20a in FIG. 1A into section 16b of the detector, thereby changing the conductivity of the buffer inside section 16b. Such changes in conductivity can be detected by means of electrodes 30, 32. The bond pads 34, 36 connected respectively to electrodes 30, 32 are connected by means of respective bonding wires 54, 56 to an analysis circuit 60 in FIG. 2 for analysis of the changing conductivity of the buffer and sample components in section 16b. From the above description, it will be evident that electrodes 30, 32, bonding wires 54, 56 as well as analysis circuit 60 are substantially at a floating potential. This overcomes one of the key problems in electrochemical detection. Since detector 10 may be made in batches using conventional micromachining techniques, the construction of detector 10 is easily reproducible and electrodes can be accurately placed in the separation column.

Figure 3:
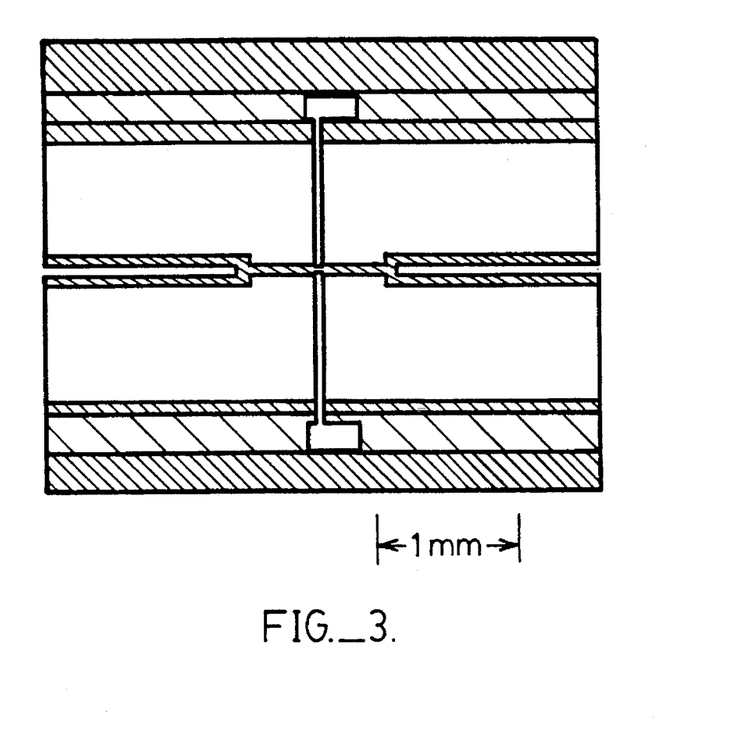
FIG. 3 is an optical micrograph of a detector, viewed through the top glass to illustrate the invention.
Figure 4:
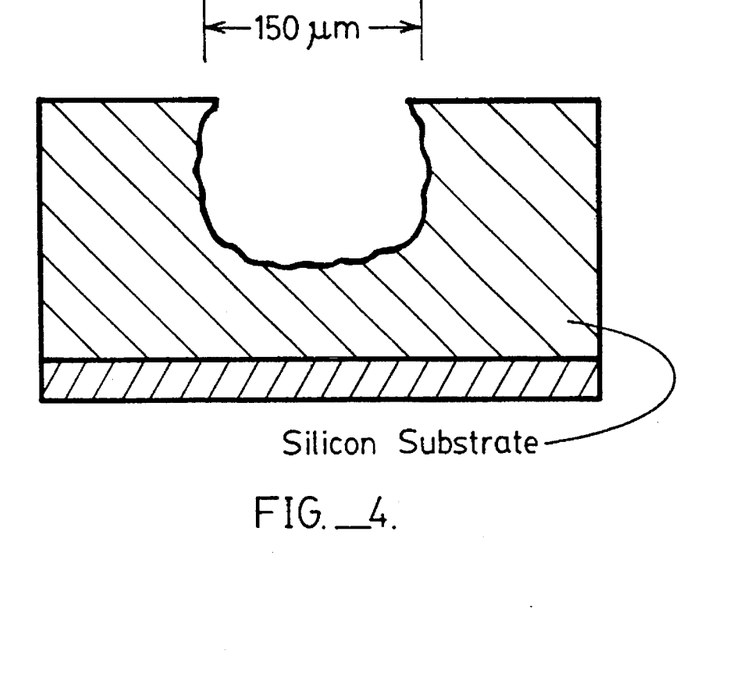
FIG. 4 is a cross-sectional view of the inlet of a detector to illustrate the invention.

FIG. 3 is an optical micrograph of a completed detector, viewed through the top glass cover to illustrate a natural embodiment of the detector 10. FIG. 4 is an optical micrograph showing a cross-sectional view of the inlet of the detector of FIG. 3.

In the embodiment FIG. 2, all of the circuitry to analyze the changes in conductivity reside in circuit 60 and detector 10 contains only the electrodes and bond pads as shown in FIGS. 1A, 1B. If desired, it would be convenient to fabricate some of the circuitry on substrate 12 using conventional semiconductor circuit fabrication techniques.

Figure 5:
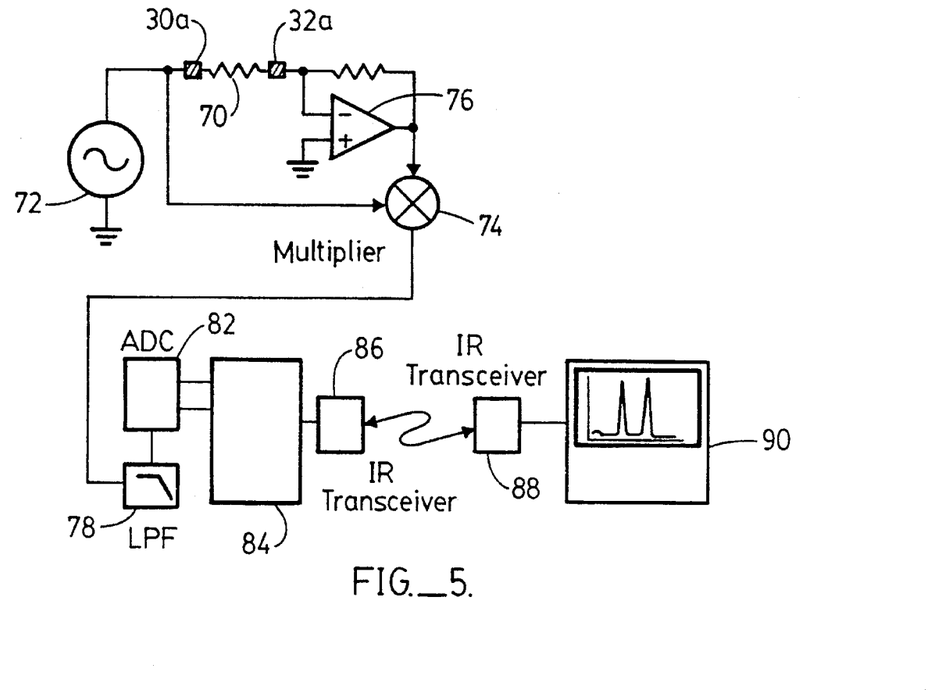
FIG. 5 is a block diagram of a conductivity-based,-optically-isolated capillary electrophoretic detection system to illustrate the preferred embodiment of the invention.
Figure 6:
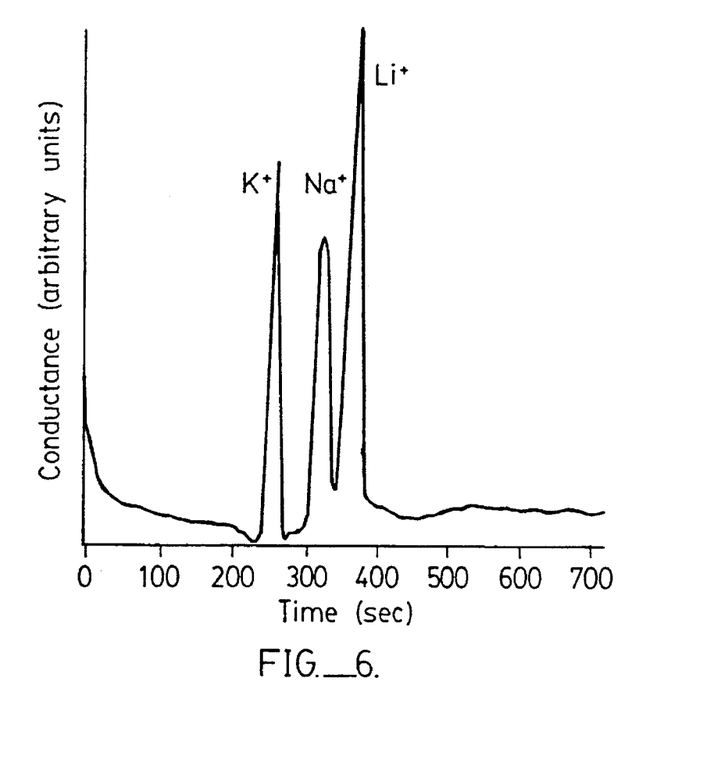
FIG. 6 is a graphical illustration of the detection results using the invention.

FIG. 5 is a block diagram of a conductivity-based,-optically-isolated capillary electrophoresis detection system to illustrate the preferred embodiment of the invention. As shown in FIG. 5, the changing impedance 70 of the buffer and sample components between the tips 30a, 32a of the electrodes at section 16b is measured using a detection circuit including circuit blocks 72, 74, 76, 78, 82, 84 and an analysis and/or storage device including block 90 of FIG. 5. An AC signal source 72 supplies an AC signal to electrode 30 and the multiplier 74. The response of impedance 70 to the signal is passed through a current-to-voltage, or transresistance amplifier 76 with negative feedback, whose output is also applied to multiplier 74. The output of multiplier 74 is passed through a low pass filter 78 and digitized by an analog-to-digital converter 82 and sampled by microcontroller 84. The serial data stream from microcontroller 84 is transformed by an infrared transceiver 86 into light signals in a manner known to those skilled in the art and transmitted to a second infrared transceiver 88 where the received light signal is converted into electrical digital signals which are then analyzed by a computer 90.

The circuit blocks 72, 74, 76, 78, 82, 84, 86 may all be fabricated on substrate 12 as indicated above. In such event, such circuitry as well as electrodes 30 and 32 are isolated electrically from transceiver 88 and computer 90. Such electrical isolation of electrodes and the associated circuitry further insulates the detection circuit. Electrodes and the associated circuitry would be operating at a floating potential determined by the potential of the electrolyte within section 16b in FIGS. 1A, 1B. Obviously, other types of optical transmission channels than infrared transceivers may be uses and are within the scope of the invention. Other electrically non-conductive communication links may also be used, such as radio signals and other transmission devices.

Materials and Methods

The electrochemical detector discussed herein is a micromachined channel that is inserted into the flow path of a conventional polyimide-coated silica capillary. The detector has a deep plasma-etched trench in a 10 mm×4 mm silicon die that is sealed with anodically bonded glass. The trench in the silicon has two widths. One region matches the 150 µm inner diameter of the capillary and acts as part of the flow channel. Platinum microelectrodes patterned on the glass are aligned to the trench to allow electrochemical sensing in the channel (FIG. 1). Standard CE capillaries are inserted into the channel and sealed with epoxy, placing the detector into the flow path (FIG. 2).

The silicon trenches were etched using a $SF_6/C_2ClF_5$ plasma to a depth of 150 µm using a two-layer AZP4620 photoresist mask. A 0.5 µm silicon dioxide layer was then thermally grown to electrically isolate the silicon substrate. Platinum electrodes and bond-pads were patterned using lift-off onto a Tempax™ glass wafer. The glass was then aligned and anodically bonded to the silicon wafer at 350° C. and 2000 V at atmospheric pressure. For access to the bond pads, trenches were etched below the bond pads during the capillary trench etch step. The resulting overhanging silicon covering the bond pads was removed during dicing to expose the pads to allow the use of a wire bonding machine for bonding to the pads. Gold bond wires 54, 56 were thermsonically bonded to the platinum pads and onto matching copper traces on a glass supporting substrate. To improve the sensitivity of conductivity measurements, amorphous ("black") platinum was electrodeposited on the platinum electrodes. This,lowered the total electrode impedance by more than an order of magnitude. Optical micrographs of the resulting structure are shown in FIGS. 3 and 4.

The electrochemical detection instrumentation has been realized with a precision battery-powered circuit. A.C. conductivity was measured with a custom designed analog lock-in amplifier and 18-bit A/D converter (FIG. 5). A microcontroller chip controls the analysis and transmits the resulting data over an infrared serial link to a personal computer running custom analysis software. Floating the instrumentation at the capillary potential allows high voltage isolation and improves power supply noise rejection.

Experimental Results

Preliminary electrophoresis experiments performed with the system show clear separation of peaks and a good signal-to-noise ratio. An analysis of a solution containing $K^+$, $Na^+$, $Li^+$ ions is shown in FIG. 5. The detection limit for these ions is better than $7\times10^{-7}M$, which is comparable to the best reported detection limits for conductivity measure. Improvement of the sensitivity is expected by using lower conductivity buffer solutions.

A microfabricated electrochemical CE detector system embodying the invention has been demonstrated. The fabrication process allows accurate, reproducible construction of a detector that is compatible with existing electrophoresis systems, so that the detector can easily be retrofitted to existing CE systems. The overall system performance was comparable to the best reported conductivity detection systems for CE.

Figure 7:
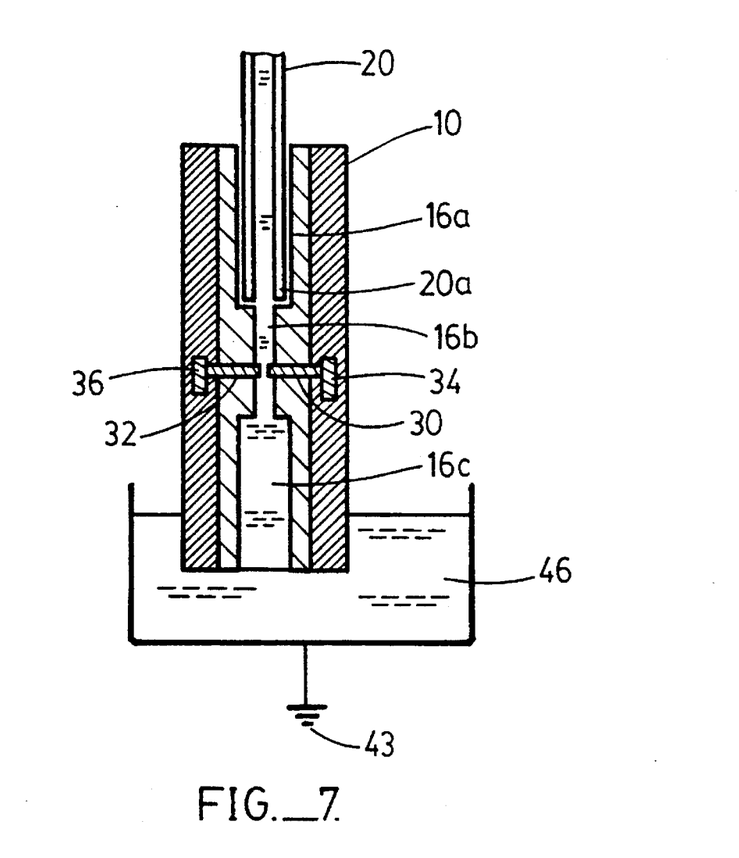
FIG. 7 is a schematic view of a portion of a modified electrophoretic separation system similar to that of FIG. 2 except for the connection of the detector to ground to illustrate an alternative embodiment.

In FIGS. 1A and 2, section 16c is connected electrically to ground through a buffer electrolyte present in capillary 22. Instead of the buffer in a capillary, other connectors, such as ionic or metallic connectors, may also be used to connect the third section 16c to ground. One alternative embodiment is shown in FIG. 7. FIG. 7 is a schematic view of a modified electrophoretic separation system different from FIG. 2 only in that the end of detector 10 containing the third section 16c is immersed in buffer reservoir 46 and capillary 22 is omitted. For simplicity, only a portion of capillary 20 is shown in FIG. 7 and bonding wires 54, 56, circuit 60, tube 44, reservoir 40 as well as high voltage 42 are omitted from FIG. 7. As shown in FIG. 7, even though capillary 22 is not used, electrical connection between section 16b and reservoir 46 is made directly by means of the buffer electrolyte present in section 16c. As will be apparent from FIG. 7, electrodes 30, 32 and bond pads 34, 36 are still at a floating electrical potential with respect to reservoir 46, ground 43 and high voltage 42, so that all of the advantages described above in reference to FIG. 2 are still present.

In the embodiments described above, the high voltage power source 42 applies the high voltage potential through end 20b of capillary 20. It will understood that such high voltage may be applied through an ionic contact through the wall of capillary 20 instead. Similarly the ground contact may also be made through an ionic contact through the wall of capillary 22 instead of through the end 22b of capillary 22.

To practice the method of this invention, one end of the capillaries such as end 20a, is inserted into section 16a. The capillary and the second section 16b are then filled with a separation medium. A sample is injected into the capillary and an electric field is applied in a section of the capillary containing the sample to cause electrophoretic separation of the sample. The separated components are then detected by means of the electrodes 30, 32.

In another method of the invention, a sample is introduced into a capillary channel containing a medium. The capillary channel may include capillary 20 as well as the second section 16b of detector 10. An electrical field is applied in a section of the channel to cause the sample to separate into its components. The pair of electrodes 30, 32 are then used to provide electrical signals in response to and indicative of the separated components. Information in the signals generated using the pair of electrodes are then transmitted through an electrically non-conductive link (e.g. optical or radio frequency link) to an analysis and/or storage device, such as computer 90.

While the invention has been described above by reference to various embodiments, it will be understood that various changes and modifications may be made without departing from the scope of invention which is to be limited only by the appended claims.

What is claimed is:

1. An apparatus for detecting components of a sample in a separation capillary system containing two capillaries and a separation medium in the capillaries, comprising:

a substrate including a micromachinable material therein, said substrate defining an elongated groove on its surface, said elongated groove having a narrower section between two wider sections;

a cover in contact with the surface of the substrate covering the groove to form an elongated tunnel, said elongated tunnel also having a narrower section between two wider sections, said two wider sections adapted to hold respective ends of the two capillaries of the separation capillary system; and one or more electrodes located at said narrower section of the tunnel, said electrodes adapted to contact a medium present in the narrower section of the tunnel.

2. The apparatus of claim 1, said material is a semiconductor material.

3. The apparatus of claim 1, said cover including a glass material.

4. The apparatus of claim 1, said electrodes being a layer of electrically conductive material on said cover or substrate.

5. The apparatus of claim 1, said wider sections having cross-sectional dimensions in a range of about 50–350 microns.

6. The apparatus of claim 1, said narrower section having cross-sectional dimensions in a range of about 25–325 microns.

7. The apparatus of claim 1, further comprising:

an electrical detection circuit responsive to electrical signals at the electrodes; and a communication link connecting the detection circuit and an analysis or storage device, said link being electrical non-conductive so that the electrodes and the detection circuit are substantially electrically isolated from the analysis or storage device.

8. The apparatus of claim 7, said link including optical transmission and reception devices.

9. The apparatus of claim 8, said devices including infrared transceivers.

10. The apparatus of claim 7, said circuit being an integrated circuit fabricated on the surface of the substrate.

11. The apparatus of claim 1, said one or more electrodes comprising two electrodes each having a tip, wherein the tips of the electrodes are located directly across the tunnel from each other, and wherein the electrode tips are in electrical communication with any medium in the narrower section of the tunnel.

12. An apparatus for electrophoretic separation of a sample and detection of the separated components, comprising:

a first and a second capillary;

a separation medium in the capillaries;

a power source; and a detector for detecting the separated components of the sample in the medium, said detector including:

(a) a housing defining an elongated tunnel therein, said tunnel having a first section with cross-sectional dimensions larger than that of the outside dimensions of the first capillary, a second elongated section with cross-sectional dimensions larger than that of the outside dimensions of the second capillary, and a third elongated section between the first and second elongated sections, said third elongated section having cross-sectional dimensions smaller than the outside dimensions of the capillaries; and (b) one or more electrodes located at said third elongated section, so that when one end of the first capillary is inserted into the first elongated section of the tunnel until said end abuts said third elongated section and when one end of the second capillary is inserted into the second elongated section of the tunnel until said end abuts said third elongated section and the third section is filled with said separation medium, said one or more electrodes is in electrical contact with said separation medium, said electrodes useful for detecting components of a sample in the medium and providing electrical signals indicative of these components; and a connector electrically connecting the medium in the second section to the source so that the power source applies an electrical field in the medium in the third section to cause electrophoretic separation of the sample into its components, and so that said electrodes are substantially at a floating potential.

13. The apparatus of claim 12, wherein said source applies an electrical potential across the medium in the two capillaries for electrophoretic separation, and wherein the electrodes are substantially at a floating potential.

14. The apparatus of claim 12, said housing comprising:

a substrate including a micromachinable material therein, said substrate defining a groove on its surface; and a cover in contact with the surface of the substrate covering the groove to form the tunnel.

15. The apparatus of claim 14, said material is a semiconductor material.

16. The apparatus of claim 14, said cover including a glass material.

17. The apparatus of claim 14, said electrodes being a layer of electrically conductive material on said cover or substrate.

18. The apparatus of claim 12, said first section having cross-sectional dimensions in a range of about 50–350 microns.

19. The apparatus of claim 12, said second section having cross-sectional dimensions in a range of about 25–325 microns.

20. The apparatus of claim 12, said detector further comprising:

an electrical detection circuit responsive to electrical signals at the electrodes indicative of the components of the sample in the medium for detecting the signals; and a communication link connecting the electrodes and an analysis or storage device, said link being electrical non-conductive so that the electrodes are substantially electrically isolated from the device.

21. The apparatus of claim 20, said link including optical transmission and reception devices.

22. The apparatus of claim 21, said devices including infrared transceivers.

23. The apparatus of claim 20, said housing including:

a substrate including a micromachinable material therein, said substrate defining a groove on its surface; and a cover in contact with the surface of the substrate covering the groove to form the tunnel, said circuit being an integrated circuit fabricated on the surface of the substrate.

24. The apparatus of claim 12, said detector comprising two electrodes each having a tip, wherein the tips of the electrodes are located directly across the tunnel from each other, and wherein the electrode tips are in electrical communication with the medium in the tunnel.

* * * * *

UNITED STATES PATENT AND TRADEMARK OFFICE
CERTIFICATE OF CORRECTION

PATENT NO. : 5,580,435
DATED : December 3, 1996
INVENTOR(S) : Gregory T.A. Kovacs It is certified that error appears in the above-indentified patent and that said Letters Patent is hereby corrected as shown below:

On the Title Page, Section [56], References Cited, OTHER PUBLICATIONS, replace the incomplete references with the completed references attached.

On the Title Page, Section [57] ABSTRACT, line 4 replace:
"separating the first and third sections with dimensions small"

with
--separating the first and third sections with dimensions smaller--

Column 1, Line 47 replace:
"The-detector of this invention enables the detection elec-"

with
--The detector of this invention enables the detection elec---

UNITED STATES PATENT AND TRADEMARK OFFICE
CERTIFICATE OF CORRECTION

PATENT NO. : 5,580,435
DATED : December 3, 1996
INVENTOR(S) : Gregory T.A. Kovacs It is certified that error appears in the above-identified patent and that said Letters Patent is hereby corrected as shown below:

Column 6, Line 5 replace:
 "platinum electrodes. This, lowered the total electrode imped-" with --platinum electrodes. This lowered the total electrode imped- --

Column 6, Line 24 replace:
 "the best reported detection limits for conductivity measure" with --the best reported detection limits for conductivity measurements--

Column 9, Line 2 in Claim 22 replace:
 "analysis or storage device, said link being electrical" with
 --analysis or storage device, said link being electrically--

UNITED STATES PATENT AND TRADEMARK OFFICE
CERTIFICATE OF CORRECTION

PATENT NO. : 5,580,435
DATED : December 3, 1996
INVENTOR(S) : Gregory T.A. Kovacs It is certified that error appears in the above-identified patent and that said Letters Patent is hereby corrected as shown below:

"Towards Miniaturized Electrophoresis and Chemical Analysis Systems on Silicon: an Alternative to Chemical Sensors," by Harrison et al., Sensors and Actuators, Vol. B10, No. 2, pp. 107-116, January 1993

"Synchronized Cyclic Capillary Electrophoresis - A Novel Approach to Ion Separations in Solution," Burggraf et al., Proceedings of Transducers '93, the 7th International Conference on Solid-State Sensors and Actuators, Institute of Electrical Engineers, Japan, pp. 399-406, Yokohama, Japan, June 7-10, 1993

"Microfabricated Electrochemical Detector for Capillary Electrophoresis", Reay et al., Proceedings of the Solid-State Sensor and Actuator Workshop, pp. 61-64, Hilton Head, SC, June 13-16, 1994

"Miniaturized Chemical Analysis Systems Based on Electrophoretic Separations and Electroosmotic Pumping", Harrison et al., Proceedings of Transducers '93, the 7th International Conference on Solid-State Sensors and Actuators, Institute of Electrical Engineers, Japan, pp. 403-406, Yokohama, Japan, June 7-10, 1993

Signed and Sealed this

Seventh Day of April, 1998

Attest:

BRUCE LEHMAN

Attesting Officer

Commissioner of Patents and Trademarks